(12) United States Patent
Pfeffer

(10) Patent No.: US 6,635,013 B2
(45) Date of Patent: Oct. 21, 2003

(54) FITNESS TRIAGE SYSTEM AND EXERCISE GETS PERSONAL

(75) Inventor: Linda Pfeffer, Los Angeles, CA (US)

(73) Assignee: Aerobics and Fitness Association of America, Sherman Oaks, CA (US)

( * ) Notice: Subject to any disclaimer, the term of this patent is extended or adjusted under 35 U.S.C. 154(b) by 284 days.

(21) Appl. No.: 09/734,413

(22) Filed: Dec. 11, 2000

(65) Prior Publication Data

US 2002/0072655 A1 Jun. 13, 2002

(51) Int. Cl.[7] ............................................. A63B 71/00
(52) U.S. Cl. ............................ 600/300; 482/8; 128/920
(58) Field of Search ................................. 482/1–9, 900, 482/902; 600/300, 301; 128/920–925

(56) References Cited

U.S. PATENT DOCUMENTS 5,692,501 A * 12/1997 Minturn ...................... 600/301
5,937,387 A * 8/1999 Summerell et al. ......... 600/301

* cited by examiner

Primary Examiner—Glenn E. Richman
(74) Attorney, Agent, or Firm—Patrick F. Bright; Bright & Lorig

(57) ABSTRACT

Exercise Gets Personal® is a system and method for delivering personalized exercise and injury prevention information based on identification and analysis of user-specific health and fitness indicators. By providing instruction for safe and effective cardiovascular, muscle conditioning and flexibility exercises, this invention assists healthy users in improving their physical fitness through exercise. The users' exercise programs are designed for safe progressions through four-week program guidelines in different levels. The Exercise Gets Personal® system is accessed by the user directly through the Internet or licensed Intranet, or through the guidance of an intake coordinator, personal trainer, or other qualified health/fitness professional.

Figure 1:
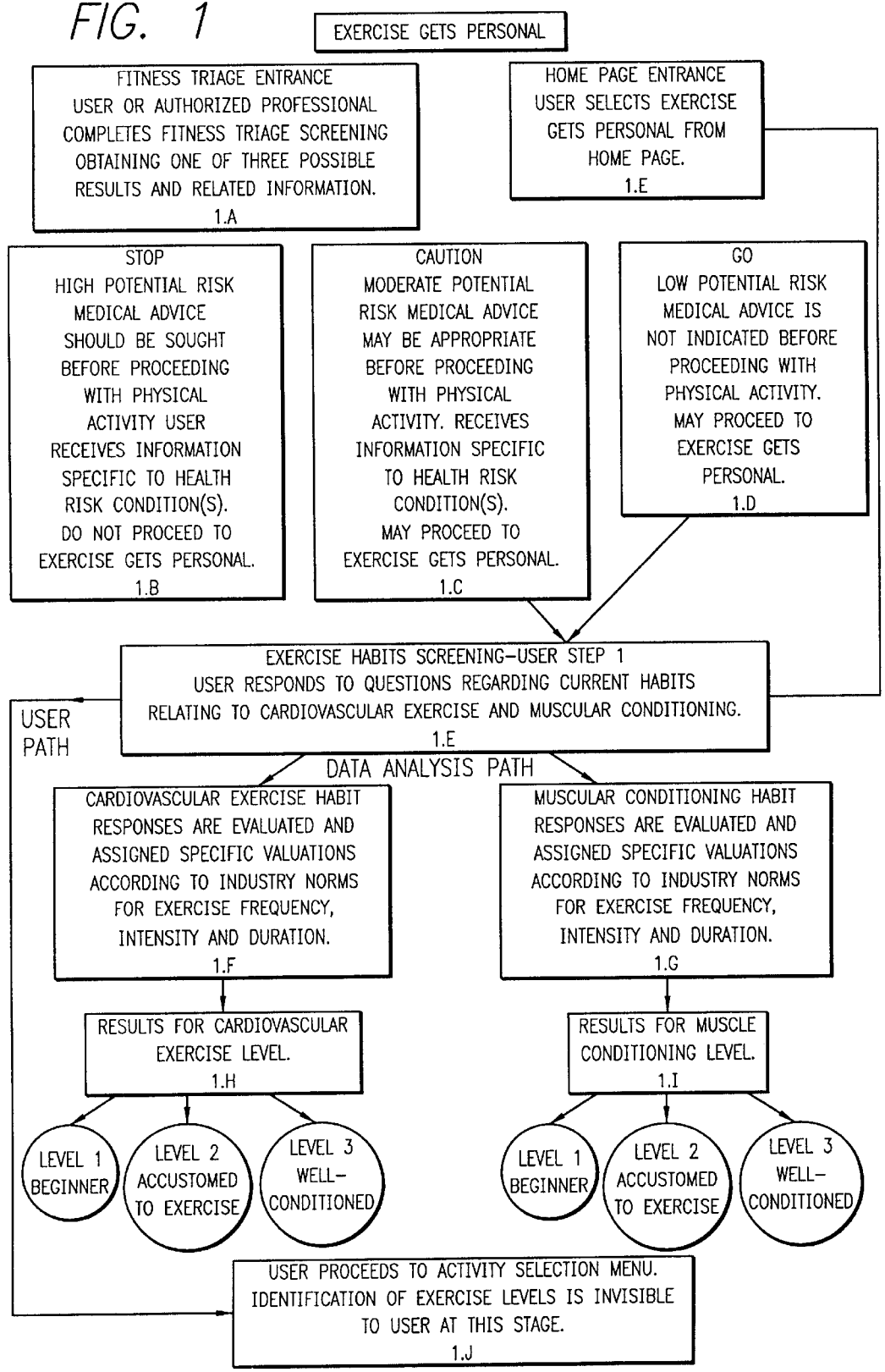

5 Claims, 2 Drawing Sheets

FITNESS TRIAGE SYSTEM AND EXERCISE GETS PERSONAL

BACKGROUND OF THE INVENTION

The invention relates to the field of exercise science and individualized instructions for exercise activity. The Exercise Gets Personal® system is integrated with the patented Fitness Triage® and Fitness Gets Personal® systems, which screen users for health risk indicators, provides appropriate information, and determines the eligibility of users for the Exercise Gets Personal® system. The purpose of integrating these systems is to identify and exclude individuals who may have medical contraindications to exercise, and who require a physician's clearance prior to starting an exercise program.

On Jul. 11, 1996, the U.S. Surgeon General's Report on Physical Activity and Health was released to the public. The publication of this report culminated over 20 years of research supporting the health risks associated with inactivity and conversely, the health benefits associated with regular exercise. Today, largely as a result of this report, every health maintenance organization and major indemnity insurer in the U.S. encourages its insured to increase physical activity as a means of promoting overall wellness and preventing disease. Additionally, since release of the Surgeon General's Report, the media has consistently delivered the message to both health providers and consumers, that exercise should be included as a part of each individual's wellness routine. However, reliable information on how to implement an individualized program of physical activity is not always available through insurance companies, health maintenance organizations, or private health care providers.

According to research, the availability of compelling data relating to the benefits of exercise is a key factor in exercise compliance. Starting and maintaining a fitness program involves behavioral changes structured to individual needs. For instance, an individual with chronic knee pain requires information and/or instruction specific to his/her condition in order to ensure that his/her exercise program is both safe and effective. Similar information is important for a wide variety of conditions such as high blood pressure, arthritis, obesity, and pregnancy. Additionally, reliable data regarding correct exercise methods is equally important to healthy individuals in both starting and maintaining an exercise program.

Prior to the introduction of the Exercise Gets Personal system, there was no program that provided individualized, evaluation and instructions for safe, progressive, goal-oriented exercise programs.

SUMMARY OF THE INVENTION

The Exercise Gets Personal® invention fills this void with a thorough, reliable system, and method of access. The system is a complete with user health risk identification screening, evaluation of current exercise activity level, selection of preferred exercise activities, precautions for contraindications to exercise, injury prevention, warm-up reasons and protocol, cardiovascular exercise programs, muscle conditioning exercise programs, and cool-down and flexibility training. The emphasis of the system is on providing safe, complete, easy-to-understand information that will assist a healthy individual in engaging in exercise activities that follow the standards and guidelines of the Aerobics and Fitness Association of America.

The invention enables the user to access this information directly or through a qualified health/fitness professional who directs the data entry. Methods of access include direct access through the Internet for a small fee associated with membership or subscription; access through an intake coordinator via phone for a small fee; and access directed by a qualified professional at a non-determined fee.

BRIEF DESCRIPTION OF THE DIAGRAMS

FIG. 1 describes the data input and analysis of the Exercise Gets Personal® system.

Figure 2:
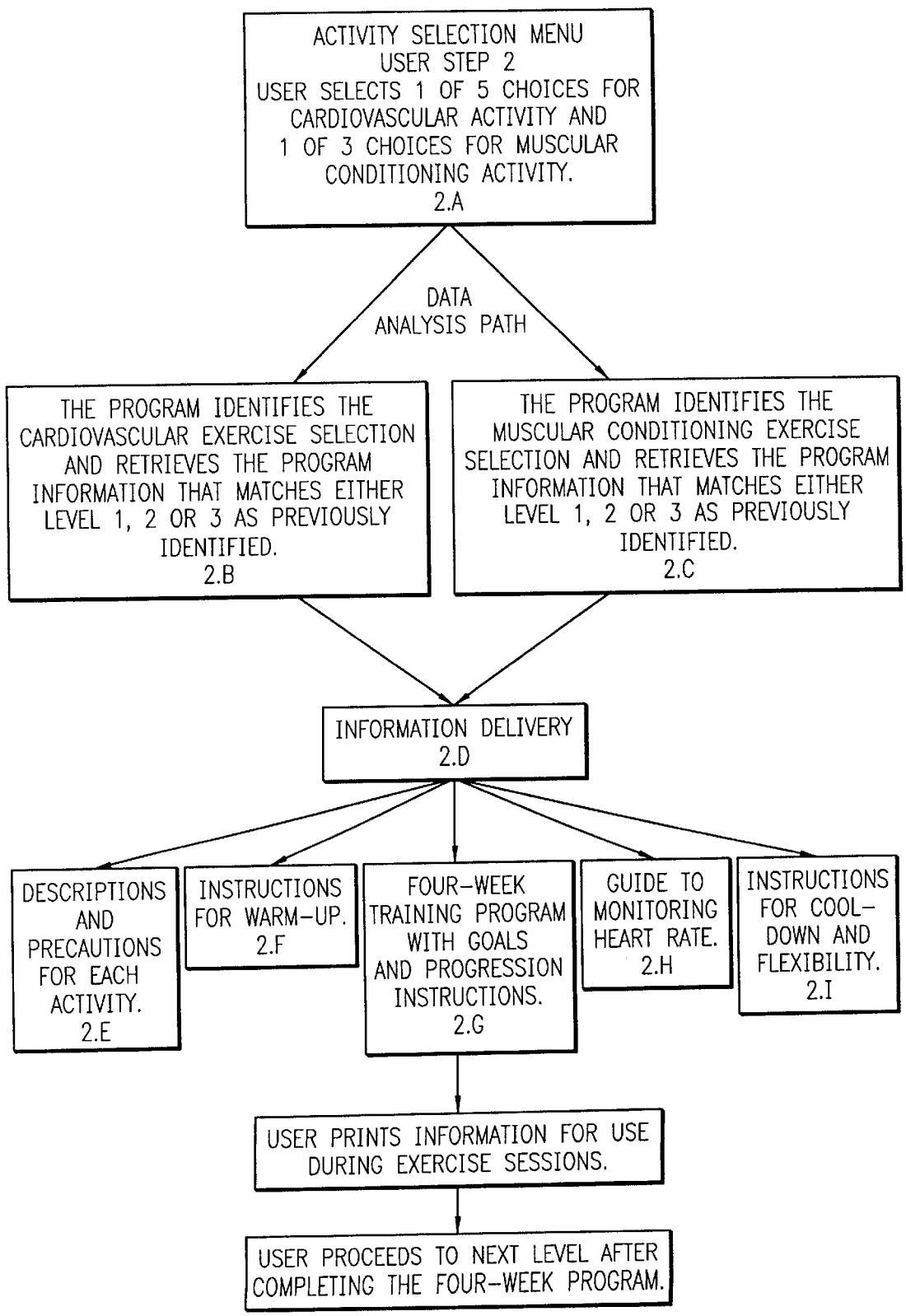

FIG. 2 describes how the system allows a user to select a preference for an activity.

1.A
  User accesses the Exercise Gets Personal® system through the Internet at the Web site of the Aerobics and Fitness Association of America (AFAA) at www.afaa.com, or through a corporate Intranet. All users are provided with a login number and password. The user may be individual obtaining information for his or her own use, or another individual, such as a fitness professional, acting on behalf of another. The entry to Exercise Gets Personal requires completion of the Fitness Triage® system process, which screens the user and identifies any health risks related to exercise. The Fitness Triage® system process evaluates the information given through the questionnaire, and assigns a category to the user based on his or her health information, and any identified risk factors. The category assigned will determine the user's eligibility for proceeding with the Exercise Gets Personal® system. One of three categories will be assigned: Stop, Caution or Go (described in 1.B through 1.D below). See U.S. Pat. No. 6,159,131, issued Dec. 12, 2000, entitled Fitness Triage System Method, and co-pending, concurrently filed U.S. patent application Ser. No. 09/734,284, entitled Fitness Triage System and Nutrition Gets Personal. The entirety of that patent is incorporated herein by reference.

1.B
  The "Stop" category is assigned to users with high potential risk. The user is advised that he or she has one or more conditions that may indicate a health problem, and is strongly advised to seek professional health care advice and a physician's clearance before attempting any physical activity. This is graphically indicated to the user with a red "Stop" button, similar to a red traffic light. The user is advised to seek professional health care advice and a physician's clearance before attempting any physical exercise activity.

1.C
  The "Caution" category is assigned to users with moderate potential risk. The user is advised that he or she has one or more conditions that may indicate a health problem, and is strongly advised to seek professional health care advice and a physician's clearance before attempting any physical activity. This is graphically indicated to the user by use of a yellow "Caution" button, similar to a yellow traffic light.

1.D
  The "Go" category is assigned to users' with low potential risk. Medical advice is not indicated before proceeding with physical activity. This is graphically indicated to the user by use of a green "Go" button, similar to a green traffic light.

1.E
  Users who receive either a "Caution" or a "Go" level of potential risk are eligible to proceed to the first user step of the Exercise Gets Personal® system. This first step is Exercise Habits Screening, which is comprised of a questionnaire that identifies the user's current physical activity habits. Specifically, the questionnaire requests information about the user's frequency, intensity, duration and mode of exercise activity for both cardiovascular exercise and muscle conditioning. The questionnaire is written in everyday language that can easily be understood by the general population.

1.F

The responses to the cardiovascular exercise section of the Exercise Habits Screening questionnaire are analyzed and assigned specific valuations according to industry norms for exercise frequency, intensity and duration.

1.G

The responses to the muscular conditioning section of the Exercise Habits Screening questionnaire are analyzed and assigned specific valuations according to industry norms for exercise frequency, intensity and duration.

1.H

Based on the above analysis, the system assigns the user to a cardiovascular exercise level appropriate to his or her current cardiovascular exercise habits. The levels are level 1: beginner, level 2: accustomed to exercise, and level 3: well conditioned.

1.I

Based on the above analysis, the system assigns the user to a muscle conditioning level appropriate to his or her current muscle conditioning exercise habits. The levels are level 1: beginner, level 2: accustomed to exercise, and level 3: well conditioned.

1.J

At this stage, the assigned exercise levels are invisible to the user. He or she is prompted to proceed to the Activity Selection menu.

2.A

The second user step in the Exercise Gets Personal® system is Activity Selection. This step allows the user to identify a preference for activity before receiving detailed instructions on how to follow the exercise program. The user is instructed to choose one of six cardiovascular exercise activities and one of three muscle conditioning activities. The available options for the cardiovascular exercise activity are: walking outdoors or indoors on a treadmill, walking/jogging outdoors or indoors on a treadmill, running outdoors or indoors on a treadmill, group exercise (including low-impact aerobics, step aerobics and cardio kickboxing), swimming, cycling outdoors or indoors and stair climber. The available options for the muscle conditioning activity are: strength training at a health club or gym, resistance tubing exercises, and exercises using light weights at home.

2.B

The system then retrieves the cardiovascular exercise program that matches the user's activity choice with his or her assigned cardiovascular exercise level.

2.C

The system then retrieves the muscle conditioning program that matches the user's activity choice with his or her assigned muscle conditioning level.

2.D

The final step is the culmination of the information gathering and analyzing process. The system delivers the user's exercise program in an easy-to-read and easy-to-understand format. At this point, the user's assigned level (1, 2 or 3) is identified to the user. The first section of information displayed for the user is a brief explanation of his or her assigned levels, and instructions on how to obtain an exercise program in the next level (for level 1 and 2 users only) after completing the four-week program.

The user is then advised to consult a physician before beginning any exercise program if he or she has not been exercising regularly. The user is advised that the Exercise Gets Personal® system is not intended as a replacement for the qualified training advice of a certified professional and is most effective when used in conjunction with a supervised fitness program. This disclaimer is provided even though the user has already indicated that he or she currently engages in exercise activity; this warning is an extra step of caution to ensure that users do not begin exercise programs inappropriately.

The last section of information preceding the exercise program description and instructions pertains to scheduling workouts. The user is advised of appropriate between-workout recovery time periods, sequencing options and program variability.

2.E

A general description of the user's cardiovascular activity is provided, along with general precautions related to hydration, gradual progression and injury prevention.

2.F

The system provides instructions and reasons for a warm-up appropriate for the chosen cardiovascular activity. The user is advised of the appropriate muscles to stretch, with guidelines for technique and duration.

2.G

The user receives two four-week exercise training programs: one for cardiovascular exercise and one for muscle conditioning. The programs are presented in easy-to-use charts that may be printed out and/or saved to the user's computer or disk. The cardiovascular exercise program is displayed on one chart, which is comprised of five columns. The left-hand column is labeled "Week #" and identifies the first, second, third and fourth weeks of the program. The other four columns display the instructions for each week's frequency, duration, intensity and goal. These factors are appropriate to the user's assigned level.

The muscle conditioning program chart is comprised of four separate charts—one for each week. The left-hand column identifies the name of an exercise. The other five columns display the instructions for frequency, number of sets, number of repetitions, weight or tube density and safety considerations. Separate from the charts are instructions on performing each of the exercises.

2.H

A guide to monitoring heart rate is provided so that the user can monitor his or her exercise intensity. The user is first provided with instructions on determining his or her target heart rate range, using the simplified Karvonen formula. Then, the user reads information about the importance of exercising within that range. Finally, the user reads instructions on counting his or her pulse at the radial artery to determine heart rate.

2.I

Instructions for cool-down and flexibility are provided, along with an explanation of the reasons for doing so.

Instructions for stretching techniques for appropriate muscles and muscle groups is provided.

What is claimed is:

1. A data processing apparatus for delivering user-specific exercise and injury prevention information comprising:

a central controller comprising a CPU and a memory operatively connected to said CPU;

at least one terminal for transmitting, to said central controller, user-specific information comprising said user's health conditions, physical exercise activities and preferences;

said memory and said central controller comprising a program, for execution by said CPU, for separately and collectively evaluating the risks associated with said user-specific information to determine whether said user may begin an exercise program and, where said user may begin such a program, what cardiovascular exercises, muscle conditioning exercises, or both, are appropriate for said user;

wherein said central controller receives said user-specific information from said terminal and outputs a statement as to whether said user may begin an exercise program, whether said user should obtain medical clearance before beginning such a program, and what cardiovascular exercises, muscle conditioning exercises, or both, are appropriate for said user, where medical clearance is not necessary.

2. The apparatus of claim 1 wherein said memory and said central controller and said program also enable a user who may begin a exercise program to access exercise information suitable for said user based on user's current habits and preferences.

3. A method of determining whether a user can begin an exercise program, and, where said user may begin such a program, for determining an appropriate exercise program for said user, using a central controller comprising a CPU, a memory operatively connected to said CPU, and a program for execution by said CPU for determining whether said user may begin such a program, and, where said user may begin, for determining an appropriate exercise program for said user, the method comprising the steps of:

inputting user-specific information about said user's cardiovascular and muscle conditioning exercises and preferences;

evaluating said user's exercises and preferences to determine said user's risks associated with said exercises and preferences; and outputting a user-appropriate exercise program comprising cardiovascular exercises, muscle conditioning exercises, or both.

4. A data processing apparatus for determining whether a user may proceed with an exercise program, and, where said user may proceed with such a program, for determining an appropriate exercise program for said user comprising:

a CPU and a memory operatively connected to said CPU, said memory comprising a program for execution by said CPU, said CPU and memory cooperating to receive user-specific inputs concerning said user's health conditions and physical exercise activities and preferences, and to determine, from said user-specific inputs, whether said user may proceed with obtaining an exercise program, and, where said user may proceed, the cardiovascular exercises, muscle conditioning exercises, or both, appropriate for said user, or whether said user should seek medical advice before beginning an exercise program.

5. A method of determining whether a user may begin an exercise program, or whether said user should first obey medical advice before beginning such a program, using a central controller comprising a CPU and a memory operatively connected to said CPU and also comprising a program for execution by said CPU for said determining steps, the method comprising the steps of:

inputting user-specific information about said user's health conditions and physical exercise activities and preferences;

individually evaluating the risk associated with said inputs;

collectively evaluating the resulting individual risks;

determining whether said user may begin an exercise program, or whether said user should obtain medical clearance before beginning an exercise program; and devising an exercise program appropriate for said user by having the CPU execute said program and output said appropriate exercise program, said exercise program including cardiovascular exercises, muscle conditioning exercises, or both, appropriate for said user.

* * * * *